United States Patent
Lin et al.

(10) Patent No.: US 6,916,177 B2
(45) Date of Patent: Jul. 12, 2005

(54) DENTAL IMPLANT WITH HARDENED CALCIUM PHOSPHATE CEMENT INSIDE

(76) Inventors: Jiin-Huey Chern Lin, 911 Tower Rd., Winnetka, IL (US) 60093; Chien-Ping Ju, 16 Pinewood Dr., Carbondale, IL (US) 62901

( * ) Notice: Subject to any disclaimer, the term of this patent is extended or adjusted under 35 U.S.C. 154(b) by 104 days.

(21) Appl. No.: 10/278,911

(22) Filed: Oct. 24, 2002

(65) Prior Publication Data

US 2004/0081941 A1 Apr. 29, 2004

(51) Int. Cl.[7] .............................................. A61C 8/00
(52) U.S. Cl. ................................. 433/173; 433/201.1
(58) Field of Search ............................. 433/176, 175, 433/220, 221, 201.1, 172, 173; 623/16.11, 11.11

(56) References Cited

U.S. PATENT DOCUMENTS

| | | | |
|---|---|---|---|
| 4,186,486 A | * | 2/1980 | Gordon .................. 433/201.1 |
| 4,379,694 A | * | 4/1983 | Riess ...................... 433/201.1 |
| 4,431,416 A | * | 2/1984 | Niznick ...................... 433/174 |
| 4,521,192 A | | 6/1985 | Linkow ...................... 433/173 |
| 5,383,935 A | | 1/1995 | Shirkhanzadeh ............. 623/16 |
| 5,639,237 A | * | 6/1997 | Fontenot ..................... 433/173 |

* cited by examiner

Primary Examiner—Melba Bumgarner
(74) Attorney, Agent, or Firm—Bacon & Thomas

(57) ABSTRACT

A dental implant. The dental implant is to be installed in a predrilled bore formed in jawbone tissue for retaining a dental prosthesis. The dental implant includes a substantially cylindrical hollow base member having a wall defining a space in the hollow base member, and through-thickness holes in communication with the space and an outer surface of the wall. Hardened calcium phosphate cement is filled in the through-thickness holes and in at least a portion of the space. A receiving member is integrally formed at one end of the hollow base member for receiving a dental prosthesis.

3 Claims, 2 Drawing Sheets

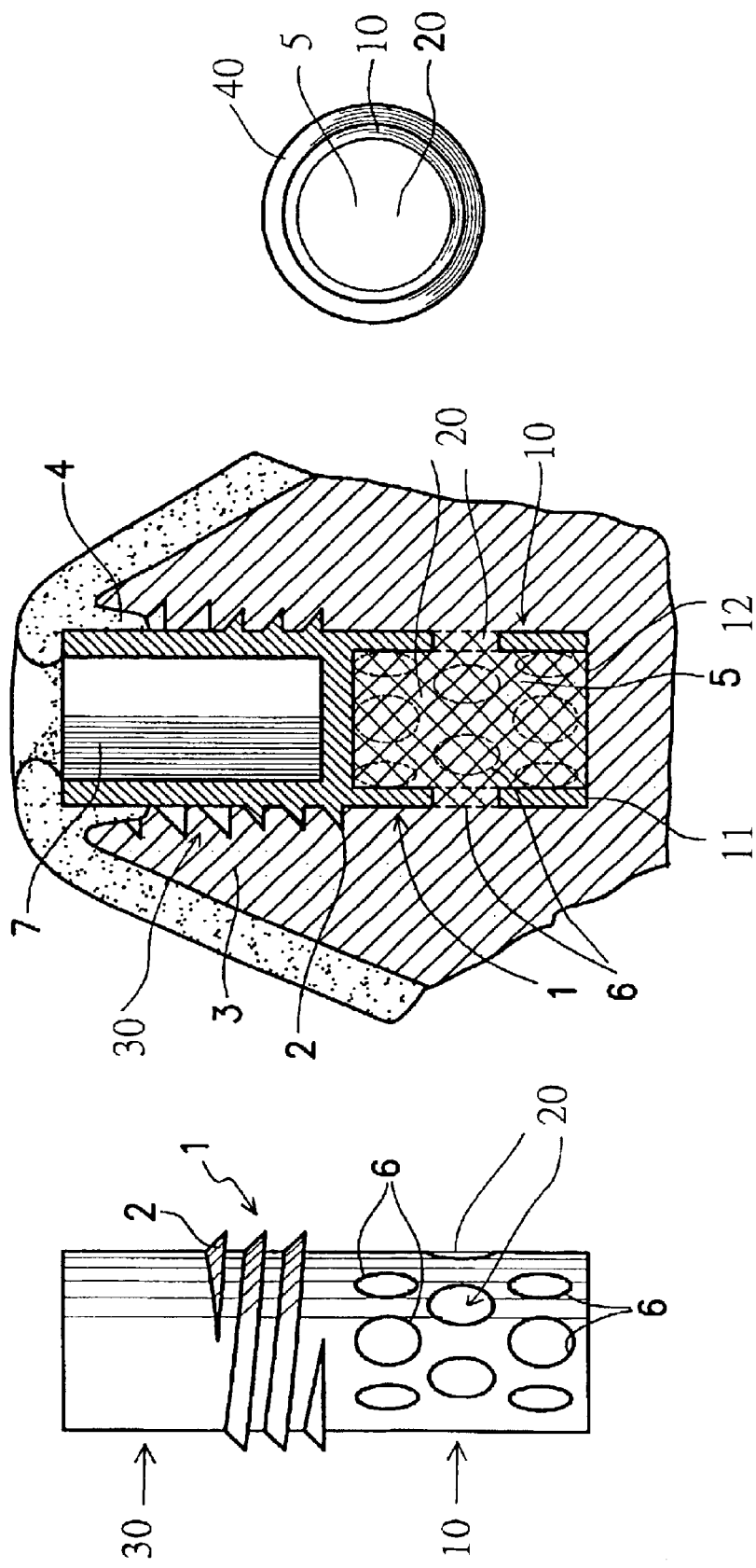

DENTAL IMPLANT WITH HARDENED CALCIUM PHOSPHATE CEMENT INSIDE

FIELD OF THE INVENTION

The present invention is related to a dental implant to be installed in a predrilled bore formed in jawbone tissue for retaining a dental prosthesis, and in particular to the dental implant with a hardened calcium phosphate cement filled in through-thickness holes and a hollow space of said dental implant.

BACKGROUND OF THE INVENTION

U.S. Pat. No. 4,521,192 discloses an oral implant allowing for the immediate installation of an artificial tooth support structure in a jawbone portion which has become oversized due to a failed prior blade implant or an enlarged tooth socket. The implant includes one or more posts upon which the artificial tooth is mounted, as well as a support structure whose lateral dimensions is sufficient to permit it to be wedged in the oversized opening. The support structure is perforated, and bone fragments or calcium phosphate are filled in the support structure.

U.S. Pat. No. 5,383,935 discloses a prosthetic implant for implantation into skeletal bone comprising an implantable base member having an internal housing surrounded partially by a porous wall, an anode secured in the internal housing in electrical contact with the porous wall, and a porous means placed in the internal housing for retaining a biocompatible electrolyte. When implanted into bone structure, the prosthetic implant generates sufficient current flow which results in in-vivo formation of calcium phosphate minerals between the implant and the surrounding bone, thereby, resulting in improved fixation and stability of the implant.

Heretofore bone graft such as calcium phosphate, calcium sulfate and bioactive glass, etc. are filled in grooves and cavities of the dental implants in the form of particles in addition to bone fragments taken from the patient during operation. Disadvantages of using particles or bone fragments in filling the dental implants include the following among others:

Low strength, so that the wall thickness of the dental implant is not able to be further reduced.

Mechanically unstable, wherein movement or micromovement of the particles or bone fragments will induce fibrous tissue not bone tissue to grow in the filled dental implants.

Leakage of the particles or bone fragments from the through-thickness holes of the filled dental implants, so that the diameter of the through-thickness holes is restricted, which adversely affects the in-growth of bone tissue.

SUMMARY OF THE INVENTION

A primary object of the present invention is to provide a dental implant free from the drawbacks of the prior art.

Another object of the present invention is to provide a dental implant which has enhanced contact between the bone graft in the dental implant and the jawbone tissue.

Another object of the present invention is to provide a dental implant which has a mechanically stable bone graft in the dental implant.

In order to achieve the aforesaid objects a dental implant constructed according to the present invention comprises:

a substantially cylindrical hollow base member comprising a wall defining a space in said base member, and a plurality of through-thickness holes communicating said space with an outer surface of said wall;

hardened calcium phosphate cement filled in said plurality of through-thickness holes and in at least a portion of said space; and a receiving member integrally formed at one end of said base member for receiving a dental prosthesis.

A suitable process for making the dental implant of the present invention comprising placing said base member of said dental implant into a mold; injecting a paste of calcium phosphate cement into said space and said plurality of through-thickness holes; setting said injected calcium phosphate cement paste for a period of time, so that said injected calcium phosphate cement paste will remain in said space and said plurality of through-thickness holes when said dental implant is separated from said mold; and separating said dental implant from said mold to obtain a hardened calcium phosphate cement filled in said plurality of through-thickness holes and in at least a portion of said space. Preferably, said hardened calcium phosphate cement is formed by further pressing said injected calcium phosphate cement paste before or during said setting.

Preferably, said base member of said dental implant has an opening at another end thereof.

Preferably, said base member of said dental implant has a perforated bottom at another end thereof.

BRIEF DESCRIPTIONS OF THE INVENTION

FIG. 1 is a side view of a dental implant constructed according to a first preferred embodiment of the present invention.

FIG. 2 is a cross-sectional view of the dental implant in FIG. 1 after it has been threaded into jawbone.

FIG. 3 is a bottom view of the dental implant in FIG. 1 and an annular mold surrounding the dental implant.

Figure 4:
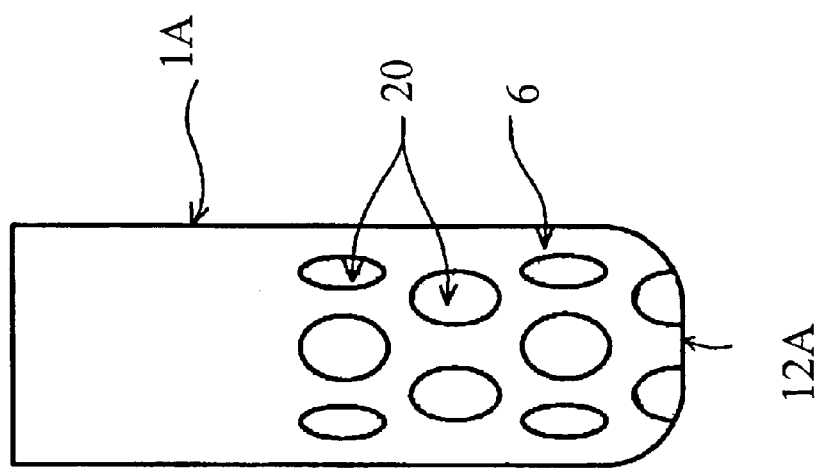

FIG. 4 a side view of a dental implant constructed according to a second preferred embodiment of the present invention.

Figure 5:
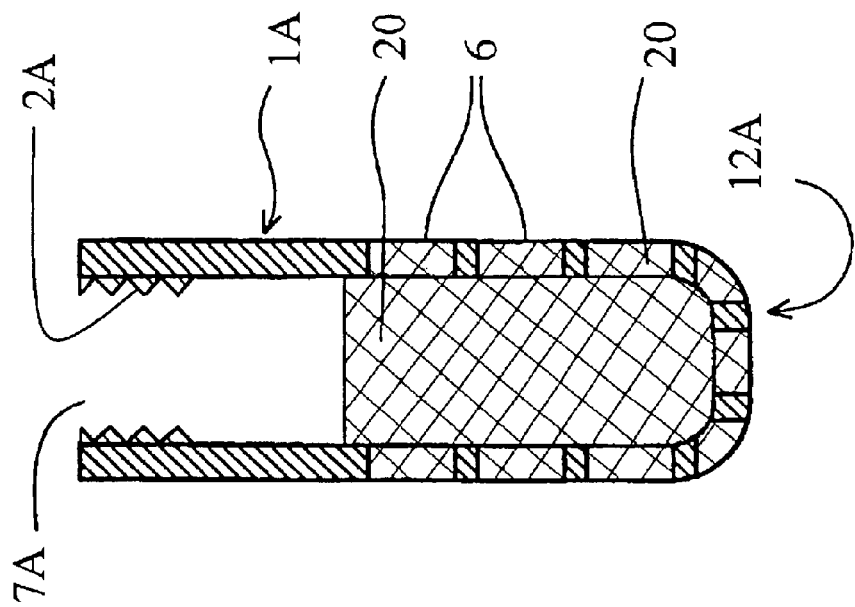

FIG. 5 is a cross-sectional view of the dental implant in FIG. 4.

DETAILED DESCRIPTION OF THE PREFERRED EMBODIMENTS

A dental implant constructed according to a first preferred embodiment of the present invention is shown in FIGS. 1, 2 and 3. The dental implant 1 is substantially cylindrical and has external threads 2 by means of which the implant is to be threaded into bone tissue 3 beneath soft tissue 4. A bore having a diameter slightly less than that of the threads 2 is drilled into the bone tissue 3, and the dental implant 1 is threaded into the bore. The dental implant 1 has a perforated tube portion 10 which is made of titanium or its alloy, and hardened calcium phosphate cement 20 filled in through holes 6 on a tube wall 11 of the perforated tube portion 10 and a space 5 inside the perforated tube portion 10. The dental implant 1 further has a receiving member 30 integrally made at a top end of said perforated tube portion 10 opposite to an open end 12 at the bottom thereof. A hexagonal hole 7 is formed in the receiving member 30, in which a dental prosthesis is to be secured.

The hardened calcium phosphate cement 20 is formed by reversing the dental implant 1 shown in FIG. 1 upside down, surrounding the perforated tube portion 10 with an annular mold 40 as shown in FIG. 3, injecting a paste of calcium phosphate cement into the space 5 until the paste reaches the upper edge of the perforated tube portion 10, pressing the injected calcium phosphate cement paste to increase the strength of the paste and assure the filling thereof in the through holes 6, setting the calcium phosphate cement paste for 1–60 minutes depending on the properties of the paste, and taking off the annular mold 40 from the dental implant 1.

Thus, the compacted and hardened calcium phosphate cement 20 is integrally formed at the through holes 6 and the space 5, as illustrated in FIG. 2.

Any calcium phosphate cement known in the art can be used in the present invention. Its technical details can be found in many patents, for examples U.S. Pat. Nos. 4,959,104; 5,092,888; 5,180,426; 5,262,166; 5,336,264; 5,525,148; 5,053,212; 5,149,368; 5,342,441; 5,503,164; 5,542,973; 5,545,254; 5,695,729 and 5,814,681.

FIGS. 4 and 5 show a dental implant 1A constructed according to a second preferred embodiment of the present invention. The dental implant 1A is in the form of a hollow cylindrical shell made of titanium or its alloy, a plurality of through holes 6 formed on a lower half of the shell body including the bottom end 12A, and an open top end 7A. Threads 2A are formed on an inner wall of an upper half of the shell body, which are used to secure a dental prosthesis. It is apparent that a mold having a shape and a size corresponding to the lower half of the shell body can be used to form a hardened calcium phosphate cement 20 in a cavity inside the lower half of the shell body and in the through holes 6 by repeating the procedures used in the first embodiment, wherein the lower half of the shell body is received in the mold and a paste of calcium phosphate cement is injected through the open top end 7A into the cavity inside the lower half of the shell body.

The dental implants made according to the first and second embodiments of the present invention have hardened calcium phosphate cement exposed to the jawbone tissue, creating a direct contact and an enlarged contact area between the hardened calcium phosphate cement and the jawbone tissue, and avoiding an adverse bone in-growth factor of bone graft movement, so that the dental implants of the present invention have an enhanced bone in-growth. Moreover, the dental implants made according to the first and second embodiments of the present invention will have an increased strength at the initial stage after they are implanted, in view of the fact that the hardened calcium phosphate cement is intimately coupled to the metallic body of the dental implant.

A third preferred embodiment of the dental implant of the present invention is similar to the second preferred embodiment except that exterior threads are provided on an outer surface of the hollow cylindrical shell for screwing into the jawbone.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A dental implant to be installed in a predrilled bore formed in jawbone tissue for retaining a dental prosthesis, said dental implant comprising:

a substantially cylindrical hollow base member comprising a wall defining a space in said substantially cylindrical hollow base member, and a plurality of through-thickness holes communicating said space with an outer surface of said wall;

wherein said base member has a bottom wall at a first end thereof, and a plurality of through-thickness holes communicating said space with an outer surface of said bottom wall;

compacted and hardened calcium phosphate cement filled in said through-thickness holes and in at least a portion of said space so that said compacted and hardened calcium phosphate cement is integrally formed at said space and said through-thickness holes; and a receiving member integrally formed at a second end of said base member for receiving a dental prosthesis.

2. The dental implant according to claim 1, wherein said hardened calcium phosphate cement is formed by placing said base member of said dental implant into a mold; injecting a paste of calcium phosphate cement into said space and said plurality of through-thickness holes; setting said injected calcium phosphate cement paste for a period of time, so that said injected calcium phosphate cement paste will remain in said space and said plurality of through-thickness holes when said dental implant is separated from said mold; and separating said dental implant from said mold.

3. The dental implant according to claim 2, wherein said hardened calcium phosphate cement is formed by further pressing said injected calcium phosphate cement paste before or during said setting.

* * * * *